United States Patent [19]

Farolfi et al.

[11] Patent Number: 5,731,302
[45] Date of Patent: Mar. 24, 1998

[54] STABLE AQUEOUS SUSPENSIONS OF MESALAZINE

[75] Inventors: Giancarlo Farolfi, Como; Franco Lattuada; Laura Ferro, both of Milan, all of Italy

[73] Assignee: Crinos Industria Farmacobiologica S.p.A., Villa Guardio, Italy

[21] Appl. No.: 722,720

[22] Filed: Sep. 30, 1996

[30] Foreign Application Priority Data

Sep. 28, 1995 [IT] Italy .................................. MI95A1987

[51] Int. Cl.$^6$ .................................................. A61K 31/615
[52] U.S. Cl. .................................................................. 514/166
[58] Field of Search ............................................ 514/166

[56] References Cited

U.S. PATENT DOCUMENTS

| 4,657,900 | 4/1987 | Powell et al. ........................ 514/166 |
| 4,664,256 | 5/1987 | Halskov ................................ 206/213 |

FOREIGN PATENT DOCUMENTS

| A 0 398 207 | 11/1990 | European Pat. Off. . |
| A 0 468 555 | 1/1992 | European Pat. Off. . |
| A-9101129 | 2/1991 | WIPO . |
| A-9212758 | 8/1992 | WIPO . |

*Primary Examiner*—Raymond Henley, III
*Attorney, Agent, or Firm*—Nikaido, Marmelstein, Murray & Oram LLP

[57] ABSTRACT

The invention discloses new compositions of mesalazine in the form of aqueous suspensions, characterized in that they are more stable than those of the prior art. The compositions contain colloidal cellulose and one or more hydrophilic thickening agents.

17 Claims, No Drawings

STABLE AQUEOUS SUSPENSIONS OF MESALAZINE

Mesalazine (D.C.I.), or mesalamine (USAN), is the internationally adopted name for 5-aminosalicylic acid or 5-ASA.

This compound is the active principle of pharmaceutical compositions for the therapy of Crohn's disease.

Pharmaceutical compositions containing this compound are usually administered rectally, in the form of enemas, in order to provide a quicker therapeutic effect, since the active principle can act directly on the intestinal mucosa from its delivery (A. B. R. Thompson "New development in the use of 5-aminosalicylic acid in patients with inflammation bowel disease" Aliment. Pharmacol. Therap. 1991; 5 449–470).

Enemas containing mesalazine are in the form of aqueous suspensions since the water solubility of the active principle is quite low at physiologic or slightly acidic pHs. As a consequence of this the main issue to be solved is that of the intrinsic lack of stability of said compositions.

The preparations of mesalazine (in the form of aqueous suspensions) disclosed in the literature of the field and/or currently sold on the market are prepared following the teachings of the art that, as shown below, don't provide a satisfactory solution regarding the stability of said compositions.

Said formulations contain thickening agents, sometimes surface active agents, and antioxidants (metabisulfite salts, usually having as the cation sodium or potassium ions), bacteriostatic and sequestering agents (EDTA). Other usual excipients are inorganic acids or acetate buffers, wherein the salt cation is sodium or potassium.

Mesalazine suspensions for topical use according to the present invention provide an expedient solution to the afore stated stability issue since they stay homogeneous longer than those of the prior art. This affords the further advantage of avoiding the patient's direct intervention for homogenizing extemporarily the formulation prior to topical application, as is recommended in the package inserts of mesalazine enemas.

According to the present invention the above discussed stability issue is solved by formulating mesalazine with selected quantities of colloidal cellulose and of hydrophilic thickening agents in aqueous suspensions.

Owing to said excipients the new liquid formulations show a thixotropic behavior.

Hence by applying a low shear to said colloidal solutions after storage for a period of time it is found that they exhibit absolute viscosities in the order of some thousands of mPa.s.

However, when they are stirred and submitted to a moderate or high rate of shear (the latter event taking place, for example, when the composition is being dispensed from a pressurized packaging or a plastic squeeze bottle), said suspensions become very flowing liquids with a viscosity of a few mPa.s.

Said latter property of being a flowing liquid is an important feature of mesalazine enemas in view of the fact that they must exhibit a very good spreading inside the large intestine (ref. I. R. Wilding et al. "Colonic spreading of a non-chlorofluorocarbon mesalazine rectal foam enema in patients with quiescent ulcerative colitis" Aliment. Pharmacol. Ther. 1995, 9, 161–166; R. A. Vitti et al. "Quantitative distribution of radiolabeled 5-aminosalicylic acid enemas in patients with leftsided ulcerative colitis" Digestive Diseases and Sciences vol. 34, 11, 1792–1797, 1989; M. Campieri et al. "Spread and distribution of 5-ASA colonic foam and 5-ASA enema in patient with ulcerative colitis" Digestive Diseases and Sciences, 37, 12, 1890–1897, 1992; M. M. C. van Buul "Retrograde spread of therapeutic enemas in patients with inflammatory bowel disease" Hepato-Gastroenterol. 36 (1989) 199–201).

In order to arrive at the present invention the applicant did thorough analytical work, performing the physical determinations and chemical analyses described below on the compositions of the prior art featured in Table 1. From said work it was determined that it is indeed desirable in this technical field to make available stable aqueous suspensions of mesalazine.

Coming now to Table 1, composition A is known from the patent application WO 92/12758 (page 18). The preparation and subsequent packaging in pressurized containers is described under example 1.

Compositions B and C are pharmaceuticals currently available in Italy.

TABLE I

Compositions of the mesalazine aqueous suspensions of the art being referred to in the disclosure of the invention.

| Excipient | Compound | Formulation A (w/w %) | Formulation B (w/v%) | Formulation C (w/w %) |
|---|---|---|---|---|
| | Mesalazine | 6.67 | 4 | 6.67 |
| THICKENING AGENT | Colloidal silica | — | 1.7 | — |
| | Xantan Gum | — | — | 0.25 |
| | Polyvinyipyrrolidone | — | 0.84 | — |
| | Carbopol ® | — | — | 0.075 |
| | Methylcellulose | — | 0.84 | — |
| | Hydroxyethylcellulose | 1.20 | — | — |
| BACTERIOSTATIC AGENT | Sodium benzoate | — | 0.38 | 0.1 |
| SEQUESTERING AGENT | EDTA disodium salt | 0.1 | — | 0.1 |
| ANTIOXIDANT | Potassium metabisulfite | — | 0.25 | 0.47 |
| | Sodium metabisulfite | 0.5 | — | — |
| | Potassium acetate | — | — | 0.41 |
| | Sodium acetate | 0.82 | — | — |
| | Phosphoric acid | — | 0.1 | — |
| | Acetic acid | enough | — | — |
| SOLVENT | Distilled water | enough to g 100 | enough to ml 100 | enough to g 60 |

TABLE I-continued

Compositions of the mesalazine aqueous suspensions of the art being referred to in the disclosure of the invention.

| Excipient | Compound | Formulation A (w/w %) | Formulation B (w/v%) | Formulation C (w/w %) |
|---|---|---|---|---|
| CONTAINER | | Pressurized aluminium container | Plastic squeeze bottle | Plastic squeeze bottle |

TABLE II

Mesalazine aqueous suspensions of the art of Table 1. Recovery tests from thereof packages and determination of the quantity of the active principle.

| | Formulation A | Formulation B | Formulation C |
|---|---|---|---|
| Time elapsed from the manufacture of the preparations under test. | 16 months | 21 months | 18 months |
| 1) Recovery of the formulation after opening the containers: | | | |
| Quantity (by weight or volume): | 61.7 g | 102 ml | 61 g |
| Active principle content (% w/w or w/v): | 6.67 | 4.08 | 6.76 |
| 2) Recovery of the formulation dispensed from the containers: | | | |
| Quantity (by weight or volume): | 59.2 g | 91.2 ml | 48.9 g |
| Ratio as % (w/w or w/v) of said quantity to that of the recovery under 1): | 95.9 | 89.4 | 80.2 |
| Active principle content (% w/w or w/v): | 5.10 | 3.84 | 7.34 |
| 3) Recovery of the formulation left in the containers after dispensing: | | | |
| Quantity (by weight or volume): | 1.98 g | 8.8 ml | 11.5 g |
| Ratio as % (w/w or w/v) of said quantity to that of the recovery under 1): | 3.2 | 8.6 | 18.8 |
| Active principle content (% w/w or w/v): | 39.30 | 7.27 | 4.43 |
| 4) Total grams recovered of the active principle/grams of mesalazine recovered under point 1): | 0.92 | 0.99 | 0.99 |

In Table II are reported the results obtained by performing the following physical determinations and chemical analyses:

A. The volume, or the corresponding weight, of the mesalazine suspension obtained by opening the container and collecting the formulation in a beaker. For formulation A and C said determination was carried out by weighing the container before and after being emptied. In the case of formulation B the density of the suspension was determined in order to convert the obtained weight into the corresponding volume.

B. HPLC assay of the active principle content in formulations A, B and C, performed as described below.

The results obtained with said analyses are given under point 1) of Table 11.

C. The weight or volume of suspension obtained by emptying the containers according to the following procedures:

By pressing the valve at the top of the container in the case of formulation A and by squeezing the plastic bottles in the case of formulations B and C The volume of formulation B was determined after assay of the bulk density.

D. The quantity of mesalazine contained in said recovered suspensions.

The results are given under point 2) of Table 11.

E. The residual volume of formulation left in the package and the quantity of the active principle contained therein (point 3 of Table 11).

The data of Table 11 represent the average of nine determinations, performed on three different samples, by repeating the assay in triplicate on each of them.

Thorough shaking of the suspensions was made prior to said determinations.

Assay of the active principle was made by HPLC on a liquid chromatograph equipped with a column Whatmann® PARTISIL® 100 SCX 25 (strong cation exchanger) length, at 25° C. and equilibrated at a flow rate of 1 ml/min. UV detector was set at a wavelength of 300 nm. The mobile phase, also referred to herein also as solvent solution or solvent, was prepared by dissolving 8.38 g $NaH_2PO_4$ in 1.9 l of bidistilled $H_2O$ and adding, when a clear solution was obtained, 80 ml of acetonitrile. pH was corrected to a value of 2.0±0.1 with concentrated phosphoric acid. The solution was brought to a volume of 2 l with bidistilled water and afterwards degassed.

The standard solution of mesalazine was prepared by weighing directly in a 50 ml volumetric flask about 46 mg of mesalazine with a known titer, and then diluting up to volume with the solvent.

The suspension thus obtained was sonicated until a clear liquid was obtained. 1 ml was diluted in a 50 ml volumetric flask up to volume with the same solvent. The sample concentration was of 0.0184 mg/ml.

For assaying mesalazine in compositions A and C, about 700 mg of each formulation (containing 46 mg of the active principle) were weighed in a 50 ml volumetric flask and diluted to volume with the mobile phase. Complete solubilization of said formulations was achieved by applying, alternately, sonication and stirring. 1 ml was pipetted out and diluted up to volume in a 50 ml volumetric flask with the solvent.

The theoretical mesalazine concentration in said samples was about the same as that of the standard solution. The standard solution and the enema samples, diluted as described above, were then injected into the liquid chromatograph.

For formulation B the analytical procedure was somewhat different. Density of the sample was determined beforehand by means of a 25 ml picnometer. The first dilution step was effected as described above for sample A and C. However, the second dilution was carried out in a 30 ml volumetric flask.

The data given in Table 11 clearly show that the prior art mesalazine aqueous suspensions become unstable, with concomitant precipitation of a solid residue containing remarkable quantities of the active principle within a period varying from 1 to 2 years. The same Table also shows that after said precipitation the concentration of the active principle in the supernatant is different from the one reported on the package label (Table I).

Regarding the compounding of aqueous suspensions for pharmaceutical use, in the book "Remington: The Science and Practice of Pharmacy—Nineteenth Edition", volume 11 pages 1515–1516 it is stated that the most important excipients of said formulations are the viscosity agents and the surface active agents, the latter being functional to wet solid particles.

In said reference are also given the following recipes, that accordingly can be used for the extemporaneous preparation of aqueous suspensions:

A. Sodium carboxymethyicellulose 2.5%, tragacanth gum 1.25% and guar gum 0.5%.

B. AVICEL® RC 591 (colloidal cellulose, a co-precipitate of microcrystalline cellulose and sodium carboxymethylcellulose) stabilized with hydroxypropylmethylcellulose, i.e. a thickening agent, being used as a suspending vehicle for propanolol and orphenadrine hydrochloride dispersions prepared from tablets.

C. CARBOPOL® 934 (acrylic acid polymer, MW≈3× $10^6$), at concentrations of 0.3% or greater, being used as a vehicle for suspending sulfamethazine 1 0% in water.

The above cited prior art provides information for compounding suspensions which do not have a long shelf life.

Regarding the recipes under points A and C, which are directed to the preparation of suspensions made using thickening agents or mixtures thereof, the applicant has determined that said excipients alone do not make mesalazine suspensions stable.

Hence even composition C, which comprises a thickening agent together with sulfamethazine, which is slightly soluble in water at neutral pH's and behaves in this aspect like mesalazine, does not provide a useful teaching for compounding a stable mesalazine liquid composition.

Regarding the inclusion of a surface active agent in the formulation, the applicant has determined that such an excipient does not influence the stability of mesalazine suspensions.

Though the recipe given under point B discloses similar excipients as those of the composition of the instant invention, formulation B does not use the proportions required in the present invention.

The following considerations are believed to be of value for determining the novelty and inventive step of the present invention in view of the prior art teachings:

1) In contrast to mesalazine, both propanolol and orphenadrine hydrochloride are soluble in water (Merck Index 10a Edition, page 7743, 7740, and page 6749–6752 respectively).

In other words, what has been suspended in the above recipe are the excipients of the tablet formulations and not the active principles. Said excipients can likely be identified as the usual water insoluble, or slightly water soluble common tablet excipients, i.e. diluents such as kaolin, starch, etc., lubricants such as magnesium or calcium stearate, etc.

2) The information provided in the above reference does not disclose any selected quantity of colloidal cellulose and hydroxypropylcellulose.

Hence the specific ranges of said components in the formulations of the instant invention could not be foreseen on the basis of said reference. Furthermore the instant limits, as it will be shown herein later on, are critical in order to ensure both the stability of the suspension and the thixotropic effect, in particular the remarkable fall of viscosity under a high rate of shear as outlined above.

EP A 0398207 discloses 5-ASA solutions containing the active principle together with its alkali metal or alkaline earth metal salt, an antioxidant and a metal complexing agent.

EP A 0468555 discloses a formulation in the form of a fluid vehicle able to generate a foam on rectal administration. Said suspension comprises at least one surfactant, a foaming propellant, a suspending or solubilizing agent for the active principle and a foam thickener.

U.S. Pat. No. 4,657,900 discloses an aqueous suspension of 5-ASA containing 0.25% bisulphite, which is stored in a single dose polyethylene bottle in a substantially oxygen-free atmosphere, the plastic bottle being hermetically sealed in a plastic pouch.

The disclosed compositions may also contain a natural or synthetic gum at concentrations from about 0.1% to 0.25% and also a flocculating agent to prevent caking of 5-ASA, such as a water gellable cross linked polyacrylic acid at a concentration of about 0.05%–0.15%.

U.S. Pat. No. 4,664,256 discloses a packaged enema solution or suspension consisting of 5-ASA, an antioxidant, a chelating agent and a buffering agent. The formulation is stored in a plastic bottle under an inert gas, and packaged in diffusion-tight light impervious bags made substantially of a plastic aluminum laminate.

WO 91/01129 discloses a solid composition for rectal administration that is reconstituted immediately before use by addition of water. Said solid composition may contain different active principles (one of which is mesalazine), an antifoam additive, a thickening agent (e.g. cellulose derivatives), and other excipients such as wetting agents, compounds for adjusting the solution isotonicity and osmolarity, diluents and low volatile liquids such as glycerine, polypropylene glycol, etc. Example 3 discloses solid compositions containing 5-ASA, sodium lauryl sulphate, hydroxypropylmethylcellulose and polydispersed silica gel. Example 4 discloses a solid composition containing 5-ASA, vinylpirrolydone/vinyl acetate copolymer, hydroxypropylmethylcellulose, sodium lauryl sulfate and an anti foaming agent.

All of the above documents fail to disclose a thickening agent in combination with colloidal cellulose, which taken together stabilize mesalazine suspensions and hence yield a homogeneous colloid system.

U.S. Pat. No. 4,657,900 discloses a thickening agent (a natural or synthetic gum) in combination with a flocculating agent, i.e. a substance which brings about flocculation or aggregation of the suspension (see "Remington's Pharmaceutical Sciences—fifteenth edition" page 325). In other words U.S. Pat. No. 4,657,900 teaches away from the present invention.

Regarding WO 91/01129, this document requires the addition of water in order to suspend the starting solid formulation. Thus this document does not disclose a stable aqueous formulation as in the present application. In order to arrive at the composition of the present invention the applicant performed stability tests on formulations obtained by modifying composition A of Table 1, which was chosen for this purpose since it was the simplest to prepare among those featured.

The modifications made were based on the teachings of the above mentioned book "Remington: The Science and Practice of Pharmacy, 19th edition".

The conclusions arrived at were the following:

It is not possible, as detailed in example 2, to make stable mesalazine aqueous suspensions using only thickening agents. It was determined that even using about twice (i.e. 2.2% w/w) the quantity of hydroxyethylcellulose as compared to that present in the original formulation A, despite the fact that the suspension thus obtained was in the form of a thick gel with an absolute viscosity value ranging in the order of some thousands mPa.s, said formulation was still unstable. It was observed that after storage in sealed glass containers at room temperature, for 1 month in the dark, a precipitate was separated.

This lack of stability was further confirmed by assaying the active principle in the supernatant gel, which titer was found to be lowered to 92.9% as compared to that of the fresh formulation.

The addition to formulation A of a surface active agent, as detailed in example 3, does not appear to significantly improve the stability of mesalazine suspensions either.

This example describes the preparation of an enema suspension obtained by increasing the quantity of hydroxyethylcellulose up to 2.0% in formulation A and then adding TWEEN® 20 in the amount of 0.25% w/w.

In this case stability was qualitatively assayed by centrifuging an aliquot of the suspension at 4000 rpm for 15 minutes and inspecting the bottom of the test tubes. The presence of a precipitate was noted. The titer of the active principle in the supernatant was found to be as low as 74.35% of the theoretical calculated based on the amount of mesalazine used in the preparation.

The problem of obtaining aqueous suspensions of mesalazine with improved stability, as compared with those of the prior art has now been solved, according to the applicant's findings, by compounding the aqueous suspensions of said active principle with a quantity of colloidal cellulose ranging from 1.2 to 1.6% (w/v of the composition), together with one or more hydrophilic thickening agents in a ratio by weight (w/w) to colloidal cellulose of between 0.04 and 0.2, corresponding respectively to a percentage of 4% and 20%. The above range becomes, or is equivalent to, 0.048–0.32% w/v when the weight of the thickening agents, calculated on the lower and upper limit of the colloidal cellulose range, is divided by the total volume of the formulation and the relevant percentages then determined.

Colloidal cellulose, otherwise defined as water dispersible cellulose, is a mixture of cellulose with 8.3–18.8% w/w of carboxymethylcellulose (Handbook of Pharmaceutical Excipients Second Edition 1994, page 86), suitable examples are AVICEL® RC 5910, AVICEL® RC 5810, AVICEL® CL-610.

The thickening agents useful in the instant invention are hydrophilic polymers such as: carboxypolymethylene, sodium carboxymethylcellulose, hydroxyethylcellulose, xantan gum, hydroxypropylmethylcellulose, methylcellulose, and carrageenan.

The suspension according to the present application preferably also contains the usual excipients such as antioxidants, sequestering and bacteriostatic agents, buffering agents, and inorganic acids. The pH is preferably between 4.5 and 5.1.

The various ranges of colloidal cellulose and of the thickening agents have been determined from the results obtained in the experiments and analytical determinations described below.

In the first set of tests, 99 different aqueous suspensions were prepared, each in the quantity of 1 liter and containing different concentrations of colloidal cellulose and of the hydrophile thickening agent. In order to prepare them nine suspensions were compounded, each containing colloidal cellulose in the relevant percentages w/v (final concentration in 1 liter) of 1; 1.1; 1.2; 1.3; 1.4; 1.5; 1.6; 1.8; and 2.0%. From each of said nine suspensions were prepared eleven further formulations containing a thickening agent (hydroxyethylcellulose) in the following relevant percentages by weight referred to colloidal cellulose: 2; 4; 6; 8; 10; 12; 14; 16; 18; 20, and 25%. Mesalazine and the other excipients were added as described in Example 4.

500 ml of each of the final 99 suspensions was transferred into capped glass containers having a diameter of 46 mm and height 56 mm (internal dimensions), while the remaining 500 ml aliquot was used to fill 20 ml syringes (Stering® Artsana, Casnate Como) having a 1.2 mm (inner diameter) ×38 mm (length) needle. The needle holder, forming one body with the flat bottom of the syringe, had an internal diameter of 2.4 mm.

Both the syringes and containers were then stored in the dark for one month at the following temperatures: 3° C., ambient temperature, 30° C. and 40° C. Inspection of the content of the glass containers at the end of this period showed that a precipitate was present at the bottom of those glass containers filled with formulations having a quantity of colloidal cellulose below 1.2% w/v. The precipitate was abundant in those suspensions conditioned at temperatures of 30° C. and 40° C.

It was also ascertained that the phenomenon was independent of the added quantity of the thickener.

It was furthermore determined that a quantity of cellulose above 1.2% w/v was not by itself enough to provide the desired stability, if concomitantly the weight ratio of the thickening agent to colloidal cellulose was not 4% or higher. In the case of 1.2% w/v of cellulose this weight ratio of the thickener to said excipient corresponds to a percentage of 0.048% w/v of the total volume solution.

It was also observed that at concentrations of colloidal cellulose higher than 1.6% w/v the suspensions retained a high viscosity and the compositions had a gel-like consistency after being manually extruded from the syringes and did not show the thixotropic behavior of the enemas of the present invention.

It was also noted that by increasing the weight ratio of the thickening agent above 20% w/w of cellulose, or above 0.32% w/v calculated on the overall suspension in the case where the colloidal cellulose quantity is 1.6% w/v, the extruded liquids resumed high values of viscosity very quickly.

This is not considered desirable in view of the fact that mesalazine enemas are generally low viscosity liquids. The results obtained in the clinical pharmacological trial reported in Example 7, demonstrate that the formulations of the present invention behave substantially as the mesalazine suspensions of the art. This suggests that the enemas of the present invention are able to retain low viscosities for a fairly long time. It was hence concluded that it is important that the new mesalazine thixotropic compositions contain colloidal cellulose and the thickening agent in appropriate quantities.

Reverting to the experiments performed by the applicant on the formulations of Example 4, worth noting is that a few syringes taken from the lots containing a quantity of colloidal cellulose between 1.2 and 1.6% and between 4% and 20% of the thickener (as percentage weight ratio to cellulose), after removal of the needle, were emptied in 4 seconds or less by applying to the plunger at a weight between about 970 and 1100 mg.

Absolute viscosity determinations performed on the same suspensions establish that the formulations satisfying the above referenced qualitative test had an absolute viscosity of 7 mPa.s or lower when measured at the shear rate of 37.6 sec-1 at a temperature of 20° C. The viscometer used was a rotational viscometer Contraves Low Shear 30 equipped with the measuring bob 1, dimensions 11×8 mm. The instrument was set on range 3, corresponding to a shear stress τ Pa 1% 0,01305. The volume of the formulations used for said determinations was about 700 µl.

Worth noting is that absolute viscosities, under the same conditions, of compositions B and C (Table 1) were very near to the above limit.

Reverting now to the further research work made on the instant formulations, in a second series of experiments it was determined in more detail, which composition of the suspension had the best behavior in the syringe test.

According to the recipe given in Example 4, were prepared 5 suspensions containing colloidal cellulose at concentrations of 1.2; 1.3; 1.4; 1.5; 1.6% w/v, respectively. From each of said suspensions were then made 7 formulations containing a quantity of hydroxyethylcellulose in the lower half of the selected range, i.e. as w/w percentage to colloidal cellulose, of 4, 5, 6, 7, 8, 9, and 10% respectively.

A total of 35 samples were prepared.

From the results obtained it was concluded that the compositions with very good thixotropic behavior and flowing properties contained 1.4% w/v of colloidal cellulose and a quantity of thickening agent varying from 6% to 7% by weight of the colloidal cellulose or, otherwise said, in a percentage w/v on the overall composition from 0.084 to 0.098% (calculated on 1.4% w/v of colloidal cellulose).

Taking into account the results obtained in the aforementioned experiments it was decided to carry out a second set of stability tests, performed at room temperature for a time longer than before, in order to check the actual shelf life of the new compositions.

Three lots of enema formulations, as shown in Table III, were prepared according to Example 5, on the basis of the indications given in Example 4.

The enemas were packed in pressurized containers under nitrogen gas by the same procedure described in the second part of Example 1. Each container was filled with a volume of enema of 60 ml, corresponding to 62 g of the formulation as established by former density determinations. Said quantity of 62 g was hence the theoretical content of each packaging on the basis of the recipe used to prepare said suspensions. The filled containers were then stored at room temperature. Three samples were then taken for analysis at time zero and then, respectively, after one and two years. The suspensions were discharged from the containers by pressing the valve stem and the weight and active principle content then determined. The weight of the residual suspension in the container was also checked. In order to carry out this latter assay the packagings were emptied by pressing the actuator, then carefully weighed, opened and washed out with water and aqueous ethanol. Afterwards they were dried in an oven at 30° C. and weighed again.

The results of stability tests are given in Table IV and provide evidence that the new compositions of mesalazine are stable for two years.

One further embodiment of the invention is the process for manufacturing the new aqueous suspensions of mesalazine.

Said process, as shown in example 6, includes the following steps:

Dissolution of colloidal cellulose and of the thickening agent in two separate aliquots of distilled water, said aliquots being 60% and 30% respectively of the total volume of water needed for the preparation of the suspension.

Mixing the two solutions and adding the other excipients of the formulation.

Adding and suspending the active principle in said solution, under vacuum and stirring.

Adding distilled water to the aqueous suspension in order to yield the final requested volume.

The new formulations may be stored in squeeze bottles containing a volume of 60 ml with 2 or 4 g of mesalazine, or in containers pressurized with nitrogen.

In the latter case particularly suitable are containers having a smaller bag filled with the suspension inside of a thin aluminum foil covered on both sides with plastic coatings.

In this way the suspension is hermetically insulated from the propellant, so that the latter is excluded from being delivered into the intestine together with the formulation during dispensing from the pressurized containers.

BRIEF DESCRIPTION OF THE DRAWINGS

FIGS. 1A, 1B and 1C show the different rheological behavior (in ordinates the shear stress in Pascal and in abscissas shear rate in s-1) of three compositions. Curve A refers to a formulation according to the instant invention having the composition of example 8, curves B and C refer to the formulations B and C featured in Table 1. Said diagrams were obtained using the same rotational viscometer (Low Shear 30) described previously, and the same volume of solution in the measuring cup. The temperature was fixed at 20° C. The range on which the instrument was set (range 5) corresponds to a shear stress τ Pa 1% 0,0326. Each point of the curve is the average of 18 separate determinations taken on the sample at intervals of 15 seconds. The sample was at first equilibrated for about 10 minutes in the measuring cup with the measuring bob dipped into the solution, rotating at the selected shear stress. Within said time readings became fairly constant. Curve A features the thixotropic properties of the suspensions according to the invention. Curves B and C show that the suspensions of the prior art containing mesalazine do not share, or share only to some extent, said property.

TABLE III

Composition w/v of the formulations used in the second series of stability tests.

| | Form. I A | Form. I B | Form. I C | Form. II A | Form. II B | Form. II C | Form. III A | Form. III B | Form. III C |
|---|---|---|---|---|---|---|---|---|---|
| Mesalazine | 6.67 | 6.67 | 6.67 | 6.67 | 6.67 | 6.67 | 6.67 | 6.67 | 6.67 |
| Colloidal cellulose (C.C.) | 1.2 | 1.2 | 1.2 | 1.4 | 1.4 | 1.4 | 1.6 | 1.6 | 1.6 |
| Hydroxyethyl cellulose (H.C.) | 0.048 | 0.084 | 0.120 | 0.056 | 0.098 | 0.140 | 0.064 | 0.112 | 0.16 |
| (H.C.)/(C.C) ratio % w/w | 4 | 7 | 10 | 4 | 7 | 10 | 4 | 7 | 10 |
| Sodium acetate | 0.8 | 0.8 | 0.8 | 0.8 | 0.8 | 0.8 | 0.8 | 0.8 | 0.8 |
| EDTA Disodium salt | 0.10 | 0.10 | 0.10 | 0.10 | 0.10 | 0.10 | 0.10 | 0.10 | 0.10 |
| Sodium metabisulfite | 0.5 | 0.5 | 0.5 | 0.5 | 0.5 | 0.5 | 0.5 | 0.5 | 0.5 |
| Acetic acid | 0.26 | 0.26 | 0.26 | 0.26 | 0.26 | 0.26 | 0.26 | 0.26 | 0.26 |

TABLE IV

Results obtained in the stability tests effected at room temperature on the compositions given in preceding Table III. Data herein provided are the average of three determinations. Abbreviations used in the Table
Form. = formulation; - Form. rec. = Formulation recovered (figures in grams) by emptying the container in a beaker after pressing the valve; - % on the theor. content = percentage by weight of the formulation recovered on the theoretical content; - Mesalazine titre = titre of mesalazine in the quantity recovered of the formulation; - Residue g. = residual grams of formulation found after opening and emptying the container.

| | Form. I A | Form. I B | Form. I C | Form. II A | Form. II B | Form. II C | Form. III A | Form. III B | Form. III C |
|---|---|---|---|---|---|---|---|---|---|
| TIME ZERO | | | | | | | | | |
| Form. rec. (g.) | 60.84 | 60.96 | 61.03 | 60.93 | 61.10 | 60.86 | 60.99 | 61.03 | 61.05 |
| % on the theor. content | 98.2 | 98.4 | 98.5 | 98.4 | 98.6 | 98.2 | 98.5 | 98.5 | 98.6 |
| Mesalazine titre | 6.66 | 6.67 | 6.67 | 6.66 | 6.68 | 6.67 | 6.67 | 6.67 | 6.67 |
| Residue g. | 0.78 | 0.74 | 0.80 | 0.75 | 0.67 | 0.77 | 0.64 | 0.82 | 0.72 |
| ONE YEAR | | | | | | | | | |
| Form. rec. (g.) | 61.06 | 60.86 | 61.13 | 60.85 | 60.98 | 60.94 | 60.85 | 61.10 | 60.88 |
| % on the theor. content | 98.6 | 98.2 | 98.7 | 98.2 | 98.4 | 98.4 | 98.2 | 98.6 | 98.5 |
| Mesalazine titre | 6.66 | 6.65 | 6.66 | 6.67 | 6.65 | 6.66 | 6.65 | 6.67 | 6.68 |
| Residue g. | 0.70 | 0.80 | 0.65 | 0.78 | 0.79 | 0.78 | 0.89 | 0.65 | 0.86 |
| TWO YEARS | | | | | | | | | |
| Form. rec. (g.) | 60.87 | 60.97 | 60.85 | 60.99 | 61.02 | 60.93 | 61.14 | 61.07 | 60.97 |
| % on the theor. content | 98.2 | 98.4 | 98.2 | 98.5 | 98.5 | 98.4 | 98.7 | 98.6 | 98.4 |
| Mesalazine titre | 6.68 | 6.67 | 6.66 | 6.65 | 6.67 | 6.67 | 6.67 | 6.67 | 6.65 |
| Residue g. | 0.80 | 0.75 | 0.83 | 0.74 | 0.78 | 0.73 | 0.65 | 0.67 | 0.80 |

Example 1

Preparation of formulation A of Table 1.

In 4.8 kg of distilled water, in a nitrogen atmosphere, were dissolved 5 g of EDTA and 41.0 g of anhydrousسodium acetate. The pH was then adjusted to 4.8 with about 19 ml of glacial acetic acid. 25 g of sodium metabisulphite was then added. The solution was transferred into a reaction vessel which was then hermetically closed. A vacuum was afterwards effected (300–400 mm Hg). Under a vigorous stirring 60 g of hydroxyethylcellulose (NATROSOL® 250HHR) was dissolved. The solution was then warmed up to 45° C. and at that temperature exhibited a gel-like consistency. The temperature was then lowered to 25°–35° C. 333.5 g of mesalazine were added. A vacuum was set up again and vigorous stirring started.

5148 g (volume about 5040 ml) of a suspension according to formulation A were obtained. The suspension was then divided into 50 packages pressurized with nitrogen gas (9–10 Atm) having a diameter of 35 mm and a volume of 110 ml. Each container was filled with 60 ml.

Example 2

Preparation of a suspension containing 6.67% (w/w) mesalazine, 2.2% of thickening agent (hydroxyethylcellulose), 0.1% disodium EDTA, 0.5% sodium metabisulphite, 0.67% sodium acetate.

Under a nitrogen atmosphere, 6 g of disodium EDTA, 40.35 g of anhydrous sodium acetate, about 17 ml of glacial acetic acid to bring the pH to 4.83, and 30 g of sodium metabisulphite were dissolved in 5.7 kg of distilled water. 120 g of hydroxyethylcellulose (NATROSOL® 250HHR) was then added with stirring and the solution was warmed at 50° C. under moderate agitation until a gel was formed, and then transferred into a vessel that was afterwards tightly closed. Vacuum was therein effected and the viscous solution was heated at 50° C. under stirring. The mass was slowly cooled and, under agitation, 400.2 g of mesalazine added. The suspension was then milled in a colloid mill and collected in a container under a nitrogen atmosphere. 5.01 kg (about 4910 ml) of the product was obtained. The assayed titer of the active principle corresponded to the theoretical.

One liter of said preparation was divided in 60 ml aliquots; into 16–100 ml glass vessels having an inner diameter of 4.6 cm (external 6 cm) and height 56 mm, afterwards the vessels were tightly sealed and stored at 25° C. in the dark. After one month three containers were taken out and carefully emptied in separate beakers. The presence of a solid residue at the bottom was observed. HPLC analysis of the active principle performed on the supernatants showed that the titer of mesalazine was 93.9% of that found at time zero.

Example 3

Preparation of a suspension containing 6.67% (w/w) mesalazine, 2% thickening agent (hydroxyethylcellulose—NATROSOL® 250HHR), 0.25% surface active agent (Tween® 20), 0.1% disodium EDTA, 0.67% sodium acetate, and 0.5% sodium metabisulphite.

In 440 g of distilled water were dissolved 1.25 g of TWEEN® 20, 0.5 g of EDTA disodium salt, and 3.36 g of anhydrous sodium acetate. The pH was corrected to 4.8 with about 1.4 ml of glacial acetic acid and 2.5 g of sodium metabisulphite was added. 10 g of hydroxyethylcellulose and then 33.33 g of the active principle were admixed and dissolved in the solution according to the procedure described in example 1. Distilled water was then added to yield 500 g. Aliquots of the freshly prepared suspension were transferred into 4–100 ml centrifuge tubes and centrifugation effected at 4000 rpm for 15 minutes. After careful removal of the supernatant a solid residue was found at the bottom of the test tubes. Said residue contained a fairly large amount of mesalazine, as shown by assaying (HPLC) the titer of the active principle in the supernatant. This residue was found to be 74.35% of that expected on the basis of the quantity used for preparing the suspension.

Example 4

Preparation of mesalazine suspensions having colloidal cellulose concentrations w/v of 1; 1.1; 1.2; 1.3; 1.4; 1.5; 1.6; 1.8 and 2.0% respectively, and thickening agent concentrations, as percentage by weight to the quantity of colloidal cellulose, of 2; 4; 6; 8; 1 0; 12; 14; 16; 18, 20 and 25% respectively, mesalazine 6.67% w/v, sodium acetate 0.8% w/v, disodium EDTA 0. 1% w/v, and sodium metabisulphite 0.5% w/v.

Each suspension was prepared in a standard quantity of 1 liter using the following procedure. 9 different suspensions of colloidal cellulose (AVICEL® RC 591) were prepared by using a 10 liter reaction vessel, into which were transferred aliquots of 7.5 liters of water to which were separately added, 125 g, 137.5 g, 150 g, 162.5 g, 175 g, 187.5 g, 200 g, 225 g, or 250 g of the above compound. Stirring was continued until a colloidal solution was obtained.

On the basis of the above colloidal cellulose quantities in a 600 ml aliquot of each of said nine suspensions were contained, respectively, 10 g, 11 g, 12 g, 13 g, 14 g, 15 g, 16 g, 18 g or 20 g of the compound.

Separately, in 300 ml aliquots of distilled water a quantity of hydroxyethylcellulose (NATROSOL® 250HHR) was dissolved in order to yield the weight ratios to colloidal cellulose discussed above. When a clear solution of the thickener had been formed, mixing was effected with the corresponding 600 ml aliquot containing the quantity of colloidal cellulose on which the amount of hydroxyethylcellulose had been calculated. To each of the solutions thus obtained were then added 8 g of anhydrous sodium acetate and 2–3 ml of glacial acetic acid. The final pH was about 4.8. 1 g of EDTA disodium salt and 5 g of sodium metabisulphite were then added.

In a nitrogen atmosphere and under stirring each solution was admixed with 66.7 g of 5-ASA, stirring was continued until a homogeneous dispersion was obtained. The suspension was then brought to the volume of 1 liter with distilled water.

Each suspension was then divided into two parts. Half were used to fill 100 ml glass containers having the dimensions set forth in Example 2. With the other half were filled syringes (syringes Steringa®, Artsana, Casnate Como) having the characteristics discussed above.

The glass containers and syringes filled with the same preparation were divided into 4 groups which were then stored, respectively, at 3° C., room temperature, 30° C. and 40° C. for one month.

At the end of the storage period the glass containers were turned carefully upside down in order to ascertain whether a precipitate had collected at the bottom, and it was found that a solid residue was present in all of those samples having a colloidal cellulose content of less than 1.2% w/v. The precipitate was particularly abundant in those samples stored at 30° C. and 40° C. The viscosities of the suspensions from which no precipitate had been separated were checked. A preliminary qualitative test was carried out by emptying the filled syringes after removal of the needle. At the same time absolute viscosity determinations were performed on some of the samples. Both assays are described above.

The formulations having a quantity of colloidal cellulose higher than 1.6% were quite viscous and in the above reported qualitative test of emptying the filled syringes did not provide the desired results.

The formulation containing a quantity of the thickening agent, given in ratio by weight to colloidal cellulose, higher than the upper limit of 20% i.e. 25%, showed a marked thixotropy since they recovered very early high viscosity values. This was considered an undesirable feature for the reasons stated above. Furthermore, it was also observed that when the ratio of the thickening agent to colloidal cellulose was below 4% the composition was not stable.

Example 5

Preparation of nine mesalazine suspensions containing colloidal cellulose in quantities respectively of 1.2; 1.4; and 1.6% w/v calculated on the overall composition, a thickening agent (hydroxyethylcellulose) in quantities of 4; 7 and 10% w/w calculated on each of the above percentages w/v of colloidal cellulose, mesalazine 6.67%, sodium acetate 0.8%, disodium EDTA 0.1%, and sodium metabisulphite 0.5%.

Each suspension was prepared in a standard quantity of 1 liter using the following procedure. Under stirring in 600 ml separate aliquots of distilled water, was suspended colloidal cellulose (AVICEL® RC 591) in the quantities, respectively, of 12 g, 14 g, and 16 g. Stirring was continued until a colloidal suspension was obtained.

For each of the above concentrations were prepared 3–600 ml samples. Separately prepared were 300 ml aqueous solutions of hydroxyethylcellulose (NATROSOL® 250HHR) containing respectively the following quantities of the compound A) 480 mg, 840 mg and 1200 mg.
B) 560, 980 and 1400 mg.
C) 640, 1120, 1600 mg.

The solutions of group A were separately admixed with 600 ml of the suspension containing 1.2% w/v colloidal cellulose.

Those of group B were separately admixed with 600 ml of the suspension containing 1.4% w/v colloidal cellulose.

Those of group C were separately admixed with 600 ml of the suspension containing 1.6% w/v colloidal cellulose.

To the suspensions thus obtained were then added 8 g of anhydrous sodium acetate and 2–3 ml of glacial acetic acid. The final pH was of about 4.8. 1 g of EDTA disodium salt and 5 g of sodium metabisulphite were then added.

In a nitrogen atmosphere and under stirring each solution was admixed with 66.7 g of 5-ASA, continuing afterwards stirring until an homogeneous dispersion was obtained, which was then brought to the volume of 1 l with distilled water.

Density determinations made with the aid of a 25 ml picnometer at the ambient temperature afforded the average value of 1.03.

Said suspensions were then transferred into pressurized packagings, each containing 60 ml of the formulations. The containers were the same as those described in example 1.

Example 6

Preparation of an industrial batch of the formulation of the invention having the following composition in 60 ml of the final product (percentages, wherein not otherwise indicated, are in w/v): Mesalazine 6.67%, colloidal cellulose 1.4%, hydroxyethylcellulose 7% w/w to colloidal cellulose, sodium acetate trihydrate 1.08%, sodium metabisulfite 0.5%, disodium EDTA 0.1%, glacial acetic acid enough to pH 4.8.

In a 600 L stainless steel reaction vessel 5.880 Kg of colloidal cellulose (AVICEL® RC 591) was suspended in 252 l of distilled water under vigorous agitation. The process was eased by operating concomitantly a colloid mill. In a different aliquot of 126 l of warm water at 45° C., in a 200 liter stainless steel vessel, were dissolved under stirring 0.411 Kg of hydroxyethylcellulose. The solution was then cooled to room temperature and added to the cellulose suspension under thorough mixing. To the resulting colloidal solution, were then added 0.420 kg of EDTA disodium salt, 4.522 Kg of sodium acetate trihydrate, and 2.100 Kg of sodium metabisufite. The vessel was then hermetically closed and vacuum was therein made (200 mm Hg). 14 Kg of mesalazine was then added under stirring. About 1 l of glacial acetic acid was then added and the solution brought to the final volume of 420 l with distilled water.

The above quantity can be used to produce 7000 pressure packings containing 60 ml each of the suspension of the invention.

Example 7

Pharmacological clinical trial with the new compositions and assessment of the distance travelled in the large intestine.

For said clinical trial the active principle 5-ASA had been radioactively labelled with 100 MegaBequerel of colloidal $^{99m}$Tc sulfide (Technetium isotope 99 sulfide). Since this salt has an half-life of only 6 hours, the compositions were radioactively labelled within 2 hours of their administration.

Twelve patients aged between 18 and 70 years were admitted to the trial, of both sexes. Admission criteria were as follows: Distal ulcerative colitis progressed up to at least 20 cm from the anus but not above the splenic flexure (established by colonoscopy at least 7 days before the beginning of the trial), low or moderate inflammation, five or more diarrhea episodes/day with blood and mucous in at least one discharge, abdominal pain, tachycardia, anemia, anorexia and vomiting.

In 6 out of 12 patients the disease was ascertained to occur in the sigmoid-rectum portion of the intestine and in the others in the colon. 48 hours before the start of the trial, therapy with sulfasalazine or other active principle related to 5-ASA was interrupted.

Each patient was administered 60 ml of the composition according to example 8 rectally.

A scintigraphic analysis was then carried out on the abdomen of the patients, kept in a prone position, respectively at 5, 30, 60, 120, 180 and 240 minutes from enema administration.

The results obtained evidenced that in 11 out of 12 patients (92%) the enema went above the sigmoid colon and in 6 patients arrived up to the transverse colon. In said latter group about 19% of the total radioactivity was still found in the transverse colon. The average time employed by the formulation to get to the point farthest from the rectum was 4 hours (3 hours for 6 patients and 6 for the other half).

Example 8

| (Composition % w/v) | |
| --- | --- |
| mesalazine | 6.67% |
| colloidal cellulose | 1.40% |
| hydroxyethylcellulose | 0.07% |
| sodium acetate trihydrate | 1.08% |
| sodium metabisulphite | 0.50% |
| EDTA disodium salt | 0.10% |
| glacial acetic acid to pH 4.6 | |
| water to 100 ml | |

Example 9

| (Composition % w/v) | |
| --- | --- |
| mesalazine | 3.33% |
| colloidal cellulose | 1.20% |
| carboxypolymethylene | 0.20% |
| sodium acetate trihydrate | 1.08% |
| sodium metabisulphite | 0.50% |
| EDTA disodium salt | 0.10% |
| glacial acetic acid to pH 4.9 | |
| water to 100 ml | |

Example 10

| (Composition % w/v) | |
|---|---|
| mesalazine | 6.67% |
| colloidal cellulose | 1.60% |
| sodium carboxymethylcellulose | 0.16% |
| sodium acetate trihydrate | 1.08% |
| sodium metabisulphite | 0.50% |
| EDTA disodium salt | 0.10% |
| glacial acetic acid to pH 5.1 | |
| water to 100 ml | |

Example 11

| (Composition % w/v) | |
|---|---|
| mesalazine | 3.33% |
| colloidal cellulose | 1.30% |
| xantan gum | 0.26% |
| sodium acetate trihydrate | 1.08% |
| sodium metabisulphite | 0.50% |
| EDTA disodium salt | 0.10% |
| glacial acetic acid to pH 4.5 | |
| water to 100 ml | |

Example 12

| (Composition % w/v) | |
|---|---|
| mesalazine | 6.67% |
| colloidal cellulose | 1.50% |
| Hydroxypropylmethylcellulose | 0.06% |
| sodium acetate trihydrate | 1.08% |
| sodium metabisulphite | 0.50% |
| EDTA disodium | 0.10% |
| glacial acetic acid to pH 4.8 | |
| water to 100 ml | |

Example 13

| (Composition % w/v) | |
|---|---|
| mesalazine | 3.33% |
| colloidal cellulose | 1.30% |
| methylcellulose | 0.10% |
| sodium acetate trihydrate | 1.08% |
| sodium metabisulfite | 0.50% |
| EDTA disodium | 0.10% |
| glacial acetic to pH 4.7 | |
| water to 100 ml | |

Example 14

| (Composition % w/v) | |
|---|---|
| mesalazine | 3.33% |
| colloidal cellulose | 1.40% |
| xantan gum | 0.21% |
| sodium acetate trihydrate | 1.08% |
| sodium metabisulphite | 0.50% |
| EDTA disodium salt | 0.1% |
| glacial acetic acid to pH 4.6 | |
| water to 60 ml | |

Example 15

| (Composition % w/v) | |
|---|---|
| mesalazine | 6.67% |
| colloidal cellulose | 1.60% |
| carboxypolymethylene | 0.32% |
| sodium acetate trihydrate | 1.08% |
| sodium metabisulphite | 0.50% |
| EDTA disodium salt | 0.10% |
| glacial acetic acid to pH 4.8 | |
| water to 100 ml | |

Example 16

Description of a pressure packaging containing an aluminum bag filled with the suspension of the invention.

Internal volume of the packaging: 110 ml (external diameter: 35 mm). Gas pressure inside (nitrogen): 9 atm. The bag made of thin aluminum foil is placed around the vertical axis of the actuator, it occupies about 60% of the total inner volume of the container and is filled with 60 ml of the suspension of the invention. The outer side of the aluminum foil is covered with propylene, the inner with polyethyleneterefialate.

We claim:

1. A pharmaceutical composition in the form of an aqueous suspension, comprising mesalazine, colloidal cellulose in an amount between 1.2 to 1.6% w/v, and at least one hydrophilic thickening agent, wherein said hydrophilic thickening agent is present in an amount of 0.048–0.32% w/v.

2. The pharmaceutial composition according to claim 1, wherein said hydrophilic thickening agent is present in a percentage by weight ratio to colloidal cellulose of between 4 and 20%.

3. The pharmaceutical composition according to claim 1, further comprising one or more excipients selected from the group consisting of sequestrants, bacteriostatic agents, antioxidants, buffering agents and inorganic acids.

4. The pharmaceutical composition according to claim 2, wherein the percentage by weight ratio of the hydrophilic thickening agent to colloidal cellulose is between 4 and 10%.

5. The pharmaceutical composition according to claim 1, wherein the percentage of colloidal cellulose is 1.4% w/v and the percentage by weight ratio of the hydrophilic thickening agent to colloidal cellulose is between 6–7%.

6. The pharmaceutical composition according to claim 1, wherein the hydrophilic thickening agent is selected from the group consisting of carboxypolymethylene, sodium carboxymethylcellulose, hydroxyethylcellulose, xantan gum, hydroxypropylmethylcellulose, methylcellulose, and carrageenan.

7. The pharmaceutical composition according to claim 6, wherein the hydrophilic thickening agent is hydroxyethylcellulose.

8. The pharmaceutical composition according to claim 1, wherein said composition is in a pressurized container which contains an inert gas as a propellant.

9. The pharmaceutical composition according to claim 8, wherein said composition is contained in a hermetically sealed bag inside the pressurized container.

10. The pharmaceutical composition according to claim 1, wherein the pH of the composition is between 4.5 and 5.1.

11. The pharmaceutical composition according to claim 1, wherein said composition exhibits the property of being stable at room temperature for a period of at least one year.

12. The pharmaceutical composition according to claim 11, wherein said composition exhibits the property of being stable at room temperature for a period of at least two years.

13. The pharmaceutical composition according to claim 1, wherein said composition is thixotropic.

14. A process for producing a stable pharmaceutical composition comprising mesalazine, colloidal cellulose in an amount between 1.2 to 1.6% w/v, and at least one hydrophilic thickening agent, wherein said hydrophilic thickening agent is present in an amount of 0.048–0.32% w/v, comprising the steps of:

a) dissolving colloidal cellulose in an aliquot of distilled water, b) dissolving a thickening agent in an aliquot of distilled water, c) mixing said colloidal cellulose and said thickening agent to produce a suspension, d) adding mesalazine to said suspension under vacuum while stirring, e) adding distilled water to the suspension to obtain the final volume.

15. A method for treating ulcerative colitis, Crohn's disease or inflammatory bowel disease, comprising administering to a patient in need of such treatment an effective amount of a pharmaceutical composition comprising mesalazine, colloidal cellulose in an amount between 1.2 to 1.6% w/v, and at least one hydrophilic thickening agent, wherein said hydrophilic thickening agent is present in an amount of 0.048–0.32% w/v.

16. The method according to claim 14, wherein said colloidal cellulose is dissolved in an aliquot of distilled water which is 60% v/v of the total volume of distilled water to be used in said composition.

17. The method according to claim 14, wherein said thickening agent is dissolved in an aliqout of distilled water which is 30% v/v of the total volume of distilled water to be used in said composition.

* * * * *